(12) United States Patent
Behar

(10) Patent No.: US 8,882,672 B2
(45) Date of Patent: *Nov. 11, 2014

(54) METHOD AND SYSTEM FOR TISSUE IMAGING AND ANALYSIS

(75) Inventor: Boaz Behar, Ganei-Tikva (IL)

(73) Assignee: Perseus-BioMed Inc., Orangeburg, NY (US)

( * ) Notice: Subject to any disclaimer, the term of this patent is extended or adjusted under 35 U.S.C. 154(b) by 341 days.

This patent is subject to a terminal disclaimer.

(21) Appl. No.: 13/519,604

(22) PCT Filed: Dec. 29, 2010

(86) PCT No.: PCT/IB2010/056117
§ 371 (c)(1),
(2), (4) Date: Jun. 28, 2012

(87) PCT Pub. No.: WO2011/080713
PCT Pub. Date: Jul. 7, 2011

(65) Prior Publication Data
US 2012/0316439 A1    Dec. 13, 2012

Related U.S. Application Data

(63) Continuation of application No. 12/648,433, filed on Dec. 29, 2009, which is a continuation-in-part of application No. 12/648,440, filed on Dec. 29, 2009.

(60) Provisional application No. 61/182,781, filed on Jun. 1, 2009, provisional application No. 61/193,815, filed on Dec. 29, 2008, provisional application No. 61/193,829, filed on Dec. 29, 2008.

(51) Int. Cl.
| | | |
|---|---|---|
| *A61B 8/00* | (2006.01) | |
| *A61B 5/01* | (2006.01) | |
| *A61N 7/02* | (2006.01) | |
| *A61B 8/08* | (2006.01) | |
| *A61B 5/145* | (2006.01) | |
| *A61B 10/02* | (2006.01) | |

(52) U.S. Cl.
CPC ............... *A61N 7/02* (2013.01); *A61B 8/0841* (2013.01); *A61B 8/085* (2013.01); *A61B 5/14532* (2013.01); *A61B 5/015* (2013.01); *A61B 8/48* (2013.01); *A61B 10/0233* (2013.01)
USPC .......................................................... 600/438

(58) Field of Classification Search
CPC ................................. A61B 5/01; A61B 8/085
USPC .......................................................... 600/438
See application file for complete search history.

(56) References Cited

U.S. PATENT DOCUMENTS

| | | |
|---|---|---|
| 4,059,010 A | 11/1977 | Sachs |
| 4,428,382 A | 1/1984 | Walsall et al. |

(Continued)

FOREIGN PATENT DOCUMENTS

| | | |
|---|---|---|
| JP | 2008-509777 | 4/2008 |
| WO | WO 03/096883 | 11/2003 |

(Continued)

OTHER PUBLICATIONS

Advisory Action Before the Filing of an Appeal Brief Dated Jan. 8, 2014 From the US Patent and Trademark Office Re. U.S. Appl. No. 12/648,440.

(Continued)

*Primary Examiner* — Jonathan Cwern

(57) ABSTRACT

A method for detecting abnormal tissue in a region of healthy tissue, comprising:
a) making a first measurement of ultrasound backscattered from the region;
b) heating the region, at least after the first measurement;
c) making one or more additional measurements of ultrasound backscattered from the region after some or all of the heating; and
d) analyzing the measurements to detect the abnormal tissue by finding one or both of differences in changes in temperature and differences in thermal expansion, caused by the heating, between the abnormal tissue and the healthy tissue.

16 Claims, 2 Drawing Sheets

(56) References Cited

U.S. PATENT DOCUMENTS

| | | | |
|---|---|---|---|
| 4,621,929 | A | 11/1986 | Phillips |
| 4,807,633 | A | 2/1989 | Fry |
| 4,995,398 | A | 2/1991 | Turnidge |
| 5,935,075 | A | 8/1999 | Casscells et al. |
| 6,728,567 | B2 | 4/2004 | Rather et al. |
| 7,211,044 | B2 | 5/2007 | Mast et al. |
| 2002/0128570 | A1 | 9/2002 | Bowman et al. |
| 2003/0171691 | A1 | 9/2003 | Casscells, III et al. |
| 2004/0030227 | A1 | 2/2004 | Littrup et al. |
| 2004/0102722 | A1 | 5/2004 | Naghavi |
| 2004/0236225 | A1 | 11/2004 | Murphy et al. |
| 2007/0106157 | A1 | 5/2007 | Kaczkowski et al. |
| 2007/0213617 | A1 | 9/2007 | Berman et al. |
| 2008/0081995 | A1 | 4/2008 | Kim et al. |
| 2008/0119729 | A1 | 5/2008 | Copa et al. |
| 2008/0200795 | A1 | 8/2008 | Steckner |
| 2008/0319355 | A1 | 12/2008 | Nita |
| 2009/0105588 | A1 | 4/2009 | Emelianov et al. |
| 2009/0287082 | A1 | 11/2009 | Lizzi et al. |

FOREIGN PATENT DOCUMENTS

| | | |
|---|---|---|
| WO | WO 2004/016177 | 2/2004 |
| WO | WO 2006/018837 | 2/2006 |
| WO | WO 2008/038182 | 4/2008 |
| WO | WO 2008/067079 | 6/2008 |
| WO | WO 2009/083973 | 7/2009 |

OTHER PUBLICATIONS

Official Action Dated Jul. 29, 2013 From the US Patent and Trademark Office Re. U.S. Appl. No. 12/648,433.

Official Action Dated Jul. 30, 2013 From the US Patent and Trademark Office Re. U.S. Appl. No. 12/648,440.

International Preliminary Report on Patentability Dated Jul. 12, 2012 From the International Bureau of WIPO Re. Application No. PCT/IB2010/056116.

Applicant-Initiated Interview Summary Dated Nov. 14, 2013 From the US Patent and Trademark Office Re. U.S. Appl. No. 12/648,440.

Applicant-Initiated Interview Summary Dated Nov. 15, 2013 From the US Patent and Trademark Office Re. U.S. Appl. No. 12/648,433.

Official Action Dated Nov. 16, 2012 From the US Patent and Trademark Office Re. U.S. Appl. No. 12/648,440.

Official Action Dated Nov. 16, 2012 From the US Patent and Trademark Office Re. U.S. Appl. No. 12/648,433.

International Search Report and the Written Opinion Dated May 23, 2011 From the International Searching Authority Re. Application No. PCT/IB2010/056117.

International Search Report and the Written Opinion Dated May 26, 2011 From the International Searching Authority Re. Application No. PCT/IB2010/056116.

Official Action Dated May 4, 2012 From the US Patent and Trademark Office Re. U.S. Appl. No. 12/648,440.

Official Action Dated May 17, 2012 From the US Patent and Trademark Office Re. U.S. Appl. No. 12/648,433.

Arthur et al. "Change in Ultrasonic Backscattered Energy for Temperature Imaging: Factors Affecting Temperature Accuracy and Spatial Resolution in 3D", 32nd UITC, 2005, 20 pages.

Bounaïm et al. "Sensitivity of the Ultrasonic CARI Technique for Breast Tumor Detection Using a FETD Scheme", Ultrasonics, 42: 919-925, 2004.

Curiel et al. "HIFU and Chemotherapy Synergistic Inhibitory Effect on Dunning AT2 Tumour-Bearing Rats", 4th International Symposium on Therapeutic Ultrasound, AIP Conference Proceedings, 754: 191-195, Mar. 28, 2005.

Despotović et al. "Using Phase Information in Ultrasound RF-Signals for Tissue Characterization", ProRISC, Nov. 2008, p. 314-317.

Dong et al. "In Vivo Measurements of Frequency-Dependent Attenuation in Tumors of the Liver", Journal of Clinical Ultrasound (JCU), 22(3): 167-174, Mar.-Apr. 1994. Abstract.

EDAP TMS "EDAP Announces Launch of Clinical Study Combining HIFU and Chemotherapy for Localized Aggressive High Risk Prostate Cancer", Bio-Medicine, 3 P., Aug. 19, 2007.

Farnoud et al. "Ultrasound Backscatter Signal Characterization and Classification Using Autoregressive Modeling and Machine Learning Algorithms", Proceedings of the 25h Annual International Conference of the IEEE EMBS Cancun, Mexico, Sep. 2003, p. 2861-2864.

Gleiter et al. "Ultrasound-Lockin-Thermography for Advanced Depth Resolved Defect Selective Imaging", ECNDT, We.3.8.2, p. 1-7, 2006.

Hollis "Non-Invasive Monitoring of Brain Tissue Temperature by Near-Infrared Spectoscopy", Thesis Submitted for the Degree of Ph.D. at the University of London, 2002, 18 pages. Abstract, acknowledgments, contents, chapter 4.

Kolios et al. "Spatial Correlation of Flow Induced Temperature Gradients During Tissue Heating with Vascular Geometry Using CT Angiography: Implications for Thermal Therapy", Physics Publications and Research, Paper 29, 1997, 3 pages.

Landini et al. "Evaluation of the Attenuation Coefficients in Normal and Pathological Breast Tissue", Medical & Biological Engineering & Computing, 24(3): 243-247, May 1986. Abstract. http://www.springerlink.com/content/h6k25vl314720870.

Liu et al. "Ultrasonic Characterization of Porcine Liver Tissue at Frequency Between 25 to 55 MHz", World Journal of Gastroenterology, 12(14): 2276-2279, Apr. 14, 2006.

O'Brien Jr. "Ultrasound-Biophysics Mechanisms", Progress in Biophysics and Molecular Biology, XP005781585, 93(1-3): 212-255, Nov. 28, 2006. Abstract, p. 235, § 2, Fig.10.

O'Brien Jr. et al. "Evaluation of the Unscanned Soft-Tissue Thermal Index", IEEE Transactions on Ultrasonics, Ferroelectrics and Frequency Control, XP011090152, 46(6): 1459-1476, Nov. 1, 1999. Abstract.

Phillips et al. "Guidance for Industry and FDA Staff. Information for Manufacturers Seeking Marketing Clearance of Diagnostic Ultrasound Systems and Transducers", Sep. 9, 2008, 68 pages.

Phillips et al. "Information for Manufacturers Seeking Marketing Clearance of Diagnostic Ultrasound Systems and Transducers", Guidance for Industry and FDA Staff, US Department for Food and Drug Administration, p. i-iv, 1-64, Sep. 9, 2008.

Rantala et al. "Lock-In Thermography With Mechanical Loss Angle Heating at Ultrasonic Frequencies", 5 P.

Seip et al. "Noninvasive Estimation of Tissue Temperature Response to Heating Fields Using Diagnostic Ultrasound", IEEE Transactions on Biomedical Engineering, 42(8): 828-839, 1995.

Seip et al. "Real-Time Detection of Multiple Lesions During High Intensity Focused Ultrasound (HIFU) Treatments", International Symposium on Therapeutic Ultrasound, Seattle, USA, 8 P. 2002.

Severcan et al. "Ultrasound Propagation Through Biological Tissues", Studia Universitatis Babes-Bolyai, Physica, Special Issue, 7 P., 2001.

Sfez et al. "Electro-Optical Ultrasound", IAEC, Annual Report, p. 1-23, 2001.

Stoner et al. "Relationship Between Blood Velocity and Conduit Artery Diameter and the Effect of Smoking on Vascular Responsiveness", Journal of Applied Physiology, 96: 2139-2145, Jun. 2004.

Straube et al. "An In Vivo System for the Determination of the Effect of Temperature on Backscattered Ultrasound Energy in Ultrasonic Images", Department of Radiation Oncology, Washington University of St. Louis.

Van Venrooij "Measurement of Ultrasound Velocity in Human Tissue", Ultrasonics, p. 240-242, Oct. 1971.

Zweschper et al. "Ultrasound Excited Thermography Using Frequency Modulated Elastics Waves", 7 P.

Notice of Reason for Rejection Dated Jul. 29, 2014 From the Japanese Patent Office Re. Application No. 2012-546549 and Its Translation Into English.

METHOD AND SYSTEM FOR TISSUE IMAGING AND ANALYSIS

RELATED APPLICATIONS

This application is a National Phase of PCT Patent Application No. PCT/IB2010/056117 having International filing date of Dec. 29, 2010, which is a continuation-in-part (CIP) of U.S. patent application Ser. Nos. 12/648,440 and 12/648,433, both filed on Dec. 29, 2009. U.S. patent application Ser. No. 12/648,440 claims the benefit of priority under 35 U.S.C. §119(e) from U.S. Provisional Patent Application No. 61/193,829 filed on Dec. 29, 2008, . U.S. patent application Ser. No. 12/648,433 claims the benefit of priority under 35 U.S.C. §119(e) from U.S. Provisional Patent Application Nos. 61/182,781 filed on Jun. 1, 2009, and 61/193,815 filed on Dec. 29, 2008. The contents of all the above application are incorporated herein by reference as if fully set forth herein.

PCT Patent Application No. PCT/IB2010/056117 is also related to PCT Patent Application No. PCT/IB2010/056116 filed on Dec. 29, 2010, the contents of which are incorporated herein by reference as if fully set forth herein.

FIELD AND BACKGROUND OF THE INVENTION

The present invention relates to measuring backscatter waveforms behavior in time due to ultrasound excitement of tissue to determine tissue type or substance composition, and more particularly, to a method, and corresponding device and system thereof, using ultrasound waves for tissue substance differential excitation, that creates different scattering behavior changes when exciting different tissues or substances; and measuring the backscatter waveform behavior before, while, and/or after excitation periods, at one or more locations in the tissue, and measuring gradients of this behavior, to image the examined area and/or determine tissue types or substance composition irregularities.

There are many situations where it is necessary or desirable to identify tissue nature and substance in an organ. One example of such a situation is the identification of malignant areas within the body of a patient, where it is required to first find the exact location of suspected cancerous region for sampling, and then indicate whether the suspected location is in fact cancerous, and if so of what malignant nature. Other such situations include the ability to visualize a map of tissue types or substance composition for medical imaging purposes. Yet another example is the need for reading different substance levels within a body, such as glucose levels in the blood.

In these and other cases it is desirable to determine tissue irregularities for localizing suspected material, image tissues, or analyze the tissue substance. It is also desirable to identify, or find the probability of identification of, tissue as of known characteristics.

Present techniques known from the prior art for determining tissue type or substance include medical imaging, and tissue sampling such as a blood sample or to biopsy techniques. Imaging of tissue type or substance and irregularities include technologies such as X-Ray, MRI, PET, Ultrasound, and IR imaging. X-Ray based tomography uses high energy electromagnetic radiation that is harmful to both patient and physician. This harmful effect substantially reduces the capacity of this technology to enable continues imagery. As X-Ray technology mainly measures acid levels in the examined area, it is limited to identifying desirable tissue differences where acid levels substantially differ. MRI uses high intensity magnetic fields. As such it yields very high cost of ownership. The need for very accurate magnetic field in MRI equipment substantially limits the geometry of the equipment, not enabling desirable physician interaction with the body of the patient at affordable costs. PET technology is limited in its capacity to identify desirable substance composition differences, and hence is used mainly in conjunction with other imaging techniques.

Ultrasound-diagnostics equipment mostly analyzes ultrasound waves' specular reflection; as such it is limited in its capacity to identify desirable tissue substance as sonic echo does not differentiate well enough between tissue materials. Table 1, a table of ultrasound speed and acoustic impedence for different soft tissues, taken from G. E. P. M. Van Venrooij, "Measurement of ultrasound velocity in human tissue," Ultrasonics, October 1971, p. 240-242, shows that specular reflection coefficients, due to differences in acoustic impedance between soft tissues, are typically only a few times $10^{-4}$, or less, which is typically below the noise level.

TABLE 1

Ultrasound velocity, density, characteristic impedance and reflection coefficient of normal brain tissue of some body fluids and brain tumors

| Substance | T [° C.] | Number of measuring points N | c [ms$^{-1}$] | error [%] | θ [kgm$^{-3}$] | Z [$10^6$ Nsm$^{-3}$] | R [×$10^5$] | Source |
|---|---|---|---|---|---|---|---|---|
| water (not degassed) | 23.5 | 20 | 1493.5 | 0.1 | 997.41 | 1.4896 | — | θ from handbook of Chemistry and Physics 1968/69 |
| blood | 23.2 | 10 | 1549.6 | 0.7 | 1036 | 1.605 | 3 | Heparinised samples from four different patients |
| blood | 24.2 | 11 | 1556.4 | 0.3 | 1041 | 1.621 | 9 | |
| blood | 22.6 | 10 | 1570 | 1.5 | 1053 | 1.653 | 43 | |
| blood | 22.4 | 12 | 1565 | 8 | 1036 | 1.62 | 11 | |
| CSF | 24.4 | 9 | 1515 | 3 | 1006 | 1.524 | 47 | Fresh samples from three different patients |
| CSF | 25 | 11 | 1509.5 | 0.5 | 1006 | 1.519 | 54 | |
| CSF | 21.8 | 11 | 1499 | 2 | 1005 | 1.506 | 62 | |
| meningioma | 19 | 20 | 1524.2 | 0.4 | — | — | — | After three hours immersion in formaline |
| meningioma | 19.8 | 20 | 1524.5 | 0.5 | 1031 | 1.572 | 0.3 | After forty-eight hours immersion in formaline |

TABLE 1-continued

Ultrasound velocity, density, characteristic impedance and reflection coefficient of normal brain tissue of some body fluids and brain tumors

| Substance | T [° C.] | Number of measuring points N | c [ms$^{-1}$] | error [%] | θ [kgm$^{-3}$] | Z [10$^6$ Nsm$^{-3}$] | R [×10$^5$] | Source |
|---|---|---|---|---|---|---|---|---|
| ependymoma | 20 | 18 | 1501 | 3 | 1024 | 1.537 | 17 | Formalised |
| astrocytoma | 24.9 | 27 | 1517 | 8 | 1079 | 1.64 | 18 | samples |
| glioma | 22.3 | 17 | 1500 | 3 | 1026 | 1.539 | 22 | |
| glioma | 22.2 | 20 | 1529.1 | 0.6 | 1021 | 1.561 | 6 | Fresh samples |
| astrocytoma | 27.5 | 41 | 1545.4 | 0.4 | — | — | — | |
| meningioma | 19.7 | 20 | 1557 | 2 | — | — | — | Five different |
| meningioma | 19.7 | 20 | 1546 | 1 | — | — | — | slides of one |
| meningioma | 19.7 | 21 | 1569 | 2 | — | — | — | tumour |
| meningioma | 19.7 | 14 | 1548 | 2 | — | — | — | |
| meningioma | 19.7 | 14 | 1569 | 2.5 | — | — | — | |

Advanced ultrasound techniques use other characteristics of the echo reflectance in the body, such as ultrasonic backscatter of power waves for elasticity measurement, however those too are not sufficient for clear differentiation between different tissue types or substances in the examined organs.

Arthur et al, in a talk "Change in Ultrasonic Backscattered Energy for Temperature Imaging: Factors Affecting Temperature Accuracy and Spatial Resolution in 3-D," presented at the 32$^{nd}$ UITC, Alexandria, Va., May 16, 2007, describe tests they did to develop a technique for using changes in backscattered energy of ultrasound to produce 3-D temperature maps in soft tissue, in order to monitor hyperthermia cancer treatment. The authors calculate theoretically that the standard deviation in backscattering energy, from place to place in a liver tissue sample with many small inclusions of aqueous or lipid material, increases monotonically with temperature, and they present in vitro test results with samples of bovine liver, turkey breast, and pork muscle, that confirm their calculations. They predict that it should be possible to use this technique to measure temperature to within 0.5 degrees Celsius, with a spatial resolution of 1 cm, for some kinds of tissue, if the tissue is calibrated.

Seip and Ebbini, "Noninvasive Estimation of Tissue Temperature Response to Heating Fields Using Diagnostic Ultrasound," IEEE Transactions on Biomedical Engineering, vol 42, pp. 828-839 (1995), describe another technique for using backscattering of diagnostic ultrasound to monitor temperature changes in tissue. The technique is based on the observation that most biological tissues are semi-regular scattering lattices. Muscle tissue, for example, may have a semi-regular lattice structure due to individual muscle fibers, with spacing on the order of 1 mm. These lattice structures produce harmonics in the backscattered ultrasound, with the frequency shift of the harmonics depending on temperature, through the temperature dependence of the sound speed, and the thermal expansion of the lattice structure. If the temperature dependence of the sound speed, and the thermal expansion coefficient, are known for the type of tissue being tested, then changes in the frequency shift can be used to measure changes in temperature. Autoregressive model-based methods are used to estimate the frequency shift. The authors state that temperature can be measured, using this technique, to within 0.4 degrees Celsius, with a spatial resolution of 1 mm. To achieve this precision, the lattice spacing, the temperature dependence of sound speed, and the thermal expansion coefficient of the tissue must all be known a priori. However, the technique could still be used to measure a relative temperature response, even if the temperature dependence of sound speed and the thermal expansion coefficient of the tissue are not known very accurately.

IR imagery is used to map the tissue's natural heat superficially, however due to the mammal natural heat control mechanisms, temperature is equalized by in-vivo tissues as heat conduction and convection occur within the organ, hence this technology is very limited in its capacity to identify desirable tissue substance.

Other means of identifying tissue substance composition include sampling tissue out of the organ for analysis. These include blood samples, biopsy, and others. The limitation of such technologies is in the need to sample out tissue from the organs, sometimes without knowing whether the sample is taken from the correct position inside the organ. Other limitations are the required handling, and the fact it is analyzed out of the living organ after loosing some of its characteristics. These currently available techniques from the prior art hence enable less than desirable functionality of real time imaging/identification or differentiation of in-vivo tissue. In particular, X-Ray harmful effects could be substantially reduced if there was to exist a harmless method for imaging in-vivo tissue at high resolution, with flexible equipment geometry, at affordable costs. Additionally, it would be preferable if there was to exist a method and system for imaging of tissue that could substantially differentiate between different tissues in an organ, and enable the identification of malignant tumors, or other irregularities in live tissue.

Blood sampling techniques known form the prior art are based on drawing of blood from the body and lack the ability of identifying the point in time where glucose levels non-linearly change from acceptable levels. In particular, the identification of time of change, could be significantly enhanced if there was to exist a capacity to conduct on going monitoring of the glucose level with non-intrusive means.

US 2004/0030227 to Littrup et al describes a method for treating a medical pathology including receiving a first set of acoustic radiation scattered by a volume of tissue containing at least a portion of the medical pathology, and thereafter, changing a temperature of the volume of tissue. The method also includes thereafter, receiving a second set of acoustic radiation scattered by the volume of tissue and localizing the portion of the medical pathology from the first and second sets of received acoustic radiation. Localizing the portion of the medical pathology comprises identifying the medical pathology from differences in the first and second sets of received acoustic radiation resulting from the change in temperature. In some embodiments, the change in temperature is produced by ultrasound heating. The method also includes insonifying the portion of the medical pathology with sufficient energy to damage the portion of the medical pathology. Littrup et al also describe heating breast tissue with RF power, and using thermoacoustic computed tomography to detect tumors, relying on the greater heating response of tumors over benign tissue.

U.S. Pat. No. 6,728,567 to Rather et al, which was a priority document for Littrup et al, describes using an array of ultrasound transducers, transmitting ultrasound through body tissue from different directions, to find the ultrasound absorption rate, the sound speed, and other parameters, as a function of three-dimensional position in the body tissue, using tomographic methods. The results are used to distinguish cancerous tissue from healthy tissue.

US 2009/0105588 to Emelianov et al, describes heating tissue with lasers, though ultrasound heating is mentioned as well, and using ultrasound to measure the temperature change and determine whether it is fat or muscle, from the fact that fat and muscle have different thermal expansion coefficients, and different rates of change of sound speed with temperature.

US 2008/0200795, to Steckner, describes applying ultrasound at the MRI resonance frequency while making an MR image, for example at 0.3 tesla, where the resonance frequency would fall within the available ultrasound frequency range. The motion of the tissue in the ultrasound fields causes motion artifacts which affect the contrast of the MR image. Differences in the contrast of the MR image at different locations can be used to obtain information about the ultrasound absorption rate at different locations, since motion artifacts will be reduced in locations where the ultrasound does not penetrate as far into the tissue, due to greater absorption of ultrasound.

US 2010/0092424 to Sanghvi et al, describes applying high intensity focused ultrasound to a tumor so that it releases cellular material, and examining the released material to determine what kind of tumor it is.

U.S. Pat. No. 7,179,449 to Lanza et al, describes using an ultrasound contrast agent that binds to a target. The contrast agent has an ultrasound reflectivity that is temperature dependent. By changing the temperature, one can distinguish reflection of the ultrasound by the contrast agent, from reflection of the ultrasound from other structures in the body.

U.S. Pat. No. 6,824,518 to Von Behren et al, describes an ultrasound imaging transducer that interleaves occasional high power pulses among normal imaging pulses, to improve image quality. The temperature is monitored while using this transducer, to avoid damage to the tissue.

U.S. Pat. No. 5,935,075, to Casscells et al, describes using an infrared sensor in a catheter, in an IR fiberoptic system, optionally combined with an ultrasound image system, which detects plaque in arteries that is likely to rupture, by the extra heat such plaque produces. The method can also detect abnormal tissue or a foreign body that is cooler than the surrounding tissue. Casscells et al cites an earlier patent, U.S. Pat. No. 4,986,671, that to describes a catheter with an infrared sensor for measuring blood flow in a blood vessel. In U.S. Pat. No. 4,621,929, infrared radiation is directed along an optical fiber to heat an infrared sensor, and its subsequent cooling rate is used to measure the blood flow.

US 2007/0106157 to Kaczkowski et al describes using backscattered ultrasound to map the temperature of tissue which has been heated using ultrasound, or using any other heat source, as a function of time. The thermal diffusivity K, which can be anisotropic in regions of dense vasculature, and the heat source Q, as functions of position, are then calculated, and they are used for planning thermal therapy. Monitoring is done in real time, during thermal therapy, to see if Q has changed, due to changes in specific absorption, or changes in the intervening path attenuation, and if so, changes can be made in the heating power in real time, to compensate. Perfusion can also be measured non-invasively, and taken into account when monitoring the thermal therapy. These methods "can also be utilized as a general tissue characterization technique", for modeling and monitoring thermal therapy.

U.S. Pat. No. 7,367,944 to Rosemberg et al describes monitoring a parameter indicating a biological response to heat, during thermal therapy, and discusses the role of perfusion in heat transport during thermal therapy.

US 2008/0004528 to Fitzsimmons et al describes using ultrasound to diagnose or characterize a target area by imaging it, to determine if it is benign or malignant, and to determine its size, geometry, vascularity, and/or density.

EP 1030611 to Baumgardner et al (CoolTouch, Inc.) describes diagnostic and therapeutic methods and techniques utilizing flushing and/or cooling, used in conjunction with energy delivery devices, including ultrasound. They describe sensing temperature, and using feedback loops for control. This is done when heating the dermis by a laser, while cooling the epidermis, in order to remove wrinkles.

US 2009/0287082 to Lizzi et al describes using ultrasound imaging to monitor heating and permanent effects in tissue, during application of therapeutic ultrasound.

SUMMARY OF THE INVENTION

There is thus a need for, and it would be highly advantageous to have a method, and corresponding device and system thereof, using ultrasonic differential backscatter analysis of ultrasound excited tissue in time, for mapping and/or identification of tissue to types or substance composition. Moreover, there is a need for such an invention which achieves high resolution, accuracy, and precision.

Additionally there is a need for such an invention that would be harmless to both physician and patient, have flexible geometry requirements enabling direct access of the physician to the patient, and enable real time imaging, and analysis of tissue types or substance composition for tissue imaging.

Additionally, there is a need for such an invention which is relatively inexpensive to construct and implement, and which is especially suitable for medical imaging.

Additionally, there is a need for such an invention which is relatively inexpensive to construct and implement, and which is especially suitable for medical analysis of in-vivo tissue.

Additionally, there is a need for such an invention which is generally applicable in blood glucose level monitoring.

Tissue substance behavior at ultrasonic excitation greatly varies at many of its characteristics. Specifically, when excited at certain frequencies, different tissues, and tissue barriers vary in their ultrasonic velocity, ultrasonic impedance, reflection coefficient, and other such parameters. In time, as energy is absorbed in the tissue, the rate of change (gradient) of these variations in time, and specifically the rate of change of the scattering coefficient, is also substantially different between tissues, and depends on the ultrasonic parameters during excitation. It has been demonstrated in multiple experiments that ultrasonic parameters such as reflectance, and velocity of different tissues greatly vary in biological tissues. It has also been demonstrated that these change when under continuous tissue excitation, as a function of tissue type, ultrasonic duration, and the ultrasonic parameters exciting the tissue. The blood system, and other biological systems equalize and regulate these changes in the tissues, and bring them back to their original levels, but despite these mechanisms, differences in backscatter behavior are equalized only minutes after ultrasonic excitation ends. It has been demonstrated in many experiments in the past, for example Arthur et al, and Seip and Ebbini, cited above, that the backscattering of ultrasonic waves is measurable, and achievable in high signal to noise ratios.

It is therefore clear from the above that it is both beneficial and possible to determine tissue type or substance and/or irregularities by inducing ultrasonic energy for excitation of the examined area and measuring the backscattering behavior and gradients of tissue locations for such determination.

In an exemplary embodiment of the invention, ultrasound waves are transmitted to the examined area. A portion of the waves' energy is continuously absorbed by the tissue material, heating it. Backscatter of ultrasound waves, either the ultrasound waves doing the heating, or other ultrasound waves used to measure the results of the heating, changes as a result of the heating. The change in backscattering characteristics may depend on the type of tissue, and on whether it is normal healthy tissue, or abnormal tissue such as cancerous tissue. This may be due to different tissues absorbing ultrasound differently, or thermally equilibrating at a different rate, resulting in a different change in temperature for different tissues, and it may also be due to the backscattering characteristics of different tissues having different dependence on temperature, for example different tissues may have different thermal expansion coefficients. The change in temperature may also depend on the frequency or mix of frequencies of waves exciting the tissue, and the corresponding amplitudes, energy levels, and the duration of ultrasonic exposure, and these effects may also be different for different tissues. The behavior of tissue at each location is measured across time, and ultrasound backscatter characteristics, such as amplitude of backscatter and the frequencies of harmonics in the backscatter, and their gradients during the excitation process are usable for determining the tissue type or substance and/or irregularities of substance levels in the tissue. The present invention is generally applicable for determining tissue material of a variety of organs, and particularly applicable for imaging of tissue areas, the identification of the location of suspected malignant (or other irregular) material, or the identification, or likelihood of specification of the malignant material itself, or the identification, or likelihood of some substance dilution factor in tissue such as glucose in blood.

The present invention relates to a method, and corresponding device and system thereof, using measurement of backscatter behavior and its gradients, from ultrasound excited tissue to image tissues of organs, and/or determine tissue irregularity, and/or determine tissue substance composition, or likelihood of being with a known substance, and/or identify the substance. Ultrasonic waves at known frequency/ frequencies with to known amplitude/amplitudes are transmitted onto a body region. The transmitted ultrasonic waves gradually cause the reflectance and other ultrasonic coefficients to change, such that parameters (backscatter frequency shift, backscatter energy, etc.) are a function of tissue substance and thermodynamic environment, frequency / frequencies of the transmitted waves, their amplitude, energy levels, and duration of the ultrasound waves. The backscattering shift and energy behavior of the excited locations changes across time: before, while, and after the excitation period such that their gradient by itself, or coupled with other measurements (such as fluid movement measurement by the ultrasound specular reflection, Doppler effect, or other imaging device) is usable for determining tissue coefficients for imaging, and for determining tissue irregularities. The backscattering behavior is also usable for determining the likelihood of the locations' tissue of being with similar characteristics to known phenomenon such as a malignancy classification.

The present invention is generally applicable for imaging of the examined area, for identifying tissue irregularities and/ or the identification of tissue material or suspected material type in the examined locations. The present invention provides an accurate and precise tissue inspection procedure. The present invention is generally applicable for identifying a biopsy location to verify biopsy sample is drawn from the location of suspected malignancy/illness area; and/or identify the type of tissue in the suspected area for its illness type; and/or indicate the likelihood of the sampled area as of being with one or more characteristics/ malignancy/ illness. The present invention may be usable in determining glucose level in the blood and/or determining the likelihood of this level being below a normal level, or being above a certain level. The present invention is relatively inexpensive to construct and implement, and is especially suitable for application in hospital equipment, medical lab equipment, medical point of care, and private medical use.

Thus, according to an exemplary embodiment of the present invention, there is provided a method using ultrasonic backscatter waveform analysis of ultrasonic excited areas for determining tissue type and or irregularity or substance level in the tissue, or likelihood of such a level featuring the main steps of: (a) exposing the examined tissue area to ultrasonic waves or multiple ultrasonic waves, each with known characteristics: (i) specific frequency (ii) specific amplitude (iii) specific energy (iv) specific duration; to such that the examined area is exited and as a result, parameters (ultrasonic backscatter pattern and energy) of the examined area are a function of the substance material composition; (c) recording one or more backscattering parameters: (i) ultrasound backscatter pattern (v) ultrasound backscatter energy at the required locations: (i) before (ii) while (iii) and after the ultrasound transmission. The parameters of the transmitted ultrasound waves and the received parameters are usable for: (i) imaging of the examined area. (ii) identify or assess the likelihood of an examined biopsy location of being of suspected material type or illness (iii) identifying irregular material of specific locations to identify required position of a biopsy.

According to another aspect of the present invention there is provided a device for differential excitation of tissues, herein, also referred to as the ultrasonic limited excitation device, that excites the diagnosed area in energy levels adequate for overcoming the natural balancing systems of the body, so as to create gradients in the scattering behavior of tissues in the examined area across more than 1% of each second, and/or for more than 200 milliseconds. The device is limited in the energy levels it transmits to the patient such that will not cause any harm or therapeutic effects, and hence is limited in not heating any portion of the examined area with more than a preset of 1 degree Celsius from its original temperature.

Alternatively, in another aspect of the present invention, there is provided such an ultrasonic limited excitation device, preset for not heating any portion of the examined area with more than a preset of 2 degree Celsius from its original temperature.

Alternatively, in another aspect of the present invention, there is provided such an ultrasonic limited excitation device, preset for not heating any portion of the examined area with more than a preset of 3-4 degree Celsius from its original temperature.

Alternatively, in another aspect of the present invention, there is provided such an ultrasonic limited excitation device, preset for not exceeding ultrasonic energy output of spatial peak temporal-average (Ispta) of 720 mW/cm^2, and mechanical index of 1.9, or spatial peak pulse-average intensity (Isppa) of 190 W/cm^2.

Alternatively, in another aspect of the present invention, there is provided such an ultrasonic limited excitation device, preset for not exceeding ultrasonic energy output of spatial peak temporal-average (Ispta) of 430 mW/cm^2, and mechanical index of 1.9, or spatial peak pulse-average intensity (Isppa) of 190 W/cm^2.

Alternatively, in another aspect of the present invention, there is provided such an ultrasonic limited excitation device, preset for not exceeding ultrasonic energy output of spatial peak temporal-average (Ispta) of 94 mW/cm^2, and mechanical index of 1.9, or spatial peak pulse-average intensity (Isppa) of 190 W/cm^2.

Alternatively, in another aspect of the present invention, there is provided such an ultrasonic limited excitation device, preset for not exceeding ultrasonic energy output of spatial peak temporal-average (Ispta) of 17 mW/cm^2, and mechanical index of 1.23, or spatial peak pulse-average intensity (Isppa) of 28 W/cm^2.

According to another aspect of the present invention there is provided a system using ultrasonic backscattering waveform analysis of ultrasonically heated areas for medical imaging and/or determining tissue type and/or irregularity and/or substance level in the tissue, or likelihood of such a level, herein, also referred to as the ultrasound excited backscatter system, of the present invention, featuring the main components of: (a) an ultrasonic heating device for differentially heating the examined tissue area; (b) an ultrasonic device, optionally separate from the ultrasonic heating device, for reading the spectral reflection of ultrasound from the tissue area, and/or the backscatter pattern and energy levels, across time as the temperature of the heated tissue changes; (c) a process control and processing unit, or a controller, operatively connected to the ultrasound transmitter/transmitters, for controlling the generation and transmission of ultrasound waves, and to the diagnostics ultrasound device, for synchronizing between the two ultrasonic transmissions (the exciting ultrasound, and the diagnostics ultrasound), and for processing the received ultrasonic waveforms and parameters in time, and analyzing data and information (backscatter shift per location, backscatter energy, etc.) generated before, while, and after the excitation, to optionally generate a graph of coefficient levels across each position in the examined area to generate a 2D, 3D, or 4D image of the examined area given the coefficients of each examined location in the examined area. The process control and data processing functions of the process control and processing unit need not be performed by a single unit, but may be distributed among two or more physically separate units, for example separate units to control a heating ultrasound transducer, and a diagnostic ultrasound transducer, and to analyze data of backscattered diagnostic ultrasound. Nevertheless, the separate units are collectively referred to herein as a controller, or a process control and processing unit.

As will be described more particularly below, the invention enables attaining one or more of the following advantages.

1. The use of an Ultrasound excited backscatter system enables accurate localization of a biopsy needle at the location of suspected malignant tissue, such that the sample is taken from an irregular substance within the organ.

2. Ultrasound excited backscatter system enables classification of suspected malignant tissue at the time of sampling.

3. The use of an Ultrasound excited backscatter system enables accurate localization of a brachytherapy needle at the location's of suspected malignant tissue, such that radioactive substance is placed at the suspected malignant tissue.

4. The use of an Ultrasound excited backscatter system enables the 2D/3D/4D imaging of soft tissue for any general radiology purposes.

There is thus provided, according to an exemplary embodiment of the invention, a method for detecting abnormal tissue in a region of healthy tissue, comprising:

a) making a first measurement of ultrasound backscattered from the region;

b) heating the region, at least after the first measurement;

c) making one or more additional measurements of ultrasound backscattered from the region after some or all of the heating; and d) analyzing the measurements to detect the abnormal tissue by finding differences in changes in temperature, caused by the heating, between the abnormal tissue and the healthy tissue.

Optionally, the measurements and analysis are sensitive enough, and the heating causes a great enough temperature rise, to detect abnormal tissue 1 centimeter in diameter in its shortest dimension, which is heated by an amount that differs by a factor of 3 from the healthy tissue.

Optionally, analyzing comprises calculating one or more characteristics of a distribution of amplitudes of backscattered ultrasound as a function of position from which it is scattered.

Additionally or alternatively, analyzing comprises calculating a frequency shift of backscattered ultrasound as a function of position from which it is scattered.

Optionally, heating comprises heating with ultrasound.

Optionally, heating with ultrasound comprises using ultrasound generated by a different ultrasound transducer than a transducer used to generate the backscattered ultrasound measured in the first and additional measurements.

Optionally, the method comprises not running the transducer used to generate the ultrasound used for heating, while making the first and additional measurements.

Optionally, heating comprises using ultrasound power that does not exceed spatial peak temporal-average (Ispta) of 720 mW/cm^2.

Optionally, heating comprises causing the temperature at each point in the region to rise by no more than 4 degrees Celsius.

In an embodiment of the invention, analyzing comprises calculating a temperature change as a function of position in the region, as a result of the heating, from the changes in the one or more ultrasound backscattering characteristics.

Optionally, the measurements are sufficiently sensitive so that analyzing the measurements can find differences in the temperature change, at different positions in the region, of less than 2 degrees Celsius, with a spatial resolution of 1 centimeter or better.

Optionally, the measurements are sufficiently sensitive so that analyzing the measurements can find the temperature change, as a function of position in the region, to within 2 degrees Celsius, with a spatial resolution of 1 centimeter or better.

Optionally, making one of more additional measurements comprises making at least two additional measurements, and analyzing comprises calculating an ultrasound absorption rate and a thermal equilibration rate as a function of position in the region.

Optionally, heating comprises heating with ultrasound power or RF power or both, and the incident ultrasound power per area, or the incident RF power per area, or both, is uniform to within a factor of 2 throughout the region, wherein the region has a cross-section of at least 3 cm by 3 cm perpendicular to the direction of incidence of the power, and extends over a distance of at least 1 cm in the direction of incidence of the power.

There if further provided, in accordance with an exemplary embodiment of the invention, a system for detecting at least one type of abnormal tissue in a region of healthy tissue, comprising:

a) a diagnostic ultrasound transducer and detector;
b) a tissue heating element, the same as or different from the diagnostic ultrasound transducer, for heating tissue; and
c) a controller programmed to:
  i) control the tissue heating element to heat the tissue in the region;
  ii) control the diagnostic ultrasound transducer and detector to make at least two measurements of backscattered ultrasound from the region, respectively before and after at least one time interval when the tissue heating element is heating the tissue in the region;
  iii) analyze results of the measurements to find differences, at different positions in the region, in the change in temperature from before to after the time interval, that distinguish that type of abnormal tissue from the healthy tissue; and
  iv) using the differences to identify which parts of the region are the abnormal tissue and which are healthy tissue.

Optionally, the tissue heating element comprises an ultrasound transducer, the same as or different from the diagnostic ultrasound transducer.

Optionally, the heating ultrasound transducer is different from the diagnostic ultrasound transducer.

Optionally, the controller is programmed to use the differences in one or more characteristics of ultrasound backscattering before and after the time interval, to find differences in one or both of a heating rate of the tissue, and a temperature equilibration rate of the tissue.

Optionally, the controller is programmed to use the differences in one or more characteristics of ultrasound backscattering to find differences in both the heating rate of the tissue, and the temperature equilibration rate of the tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
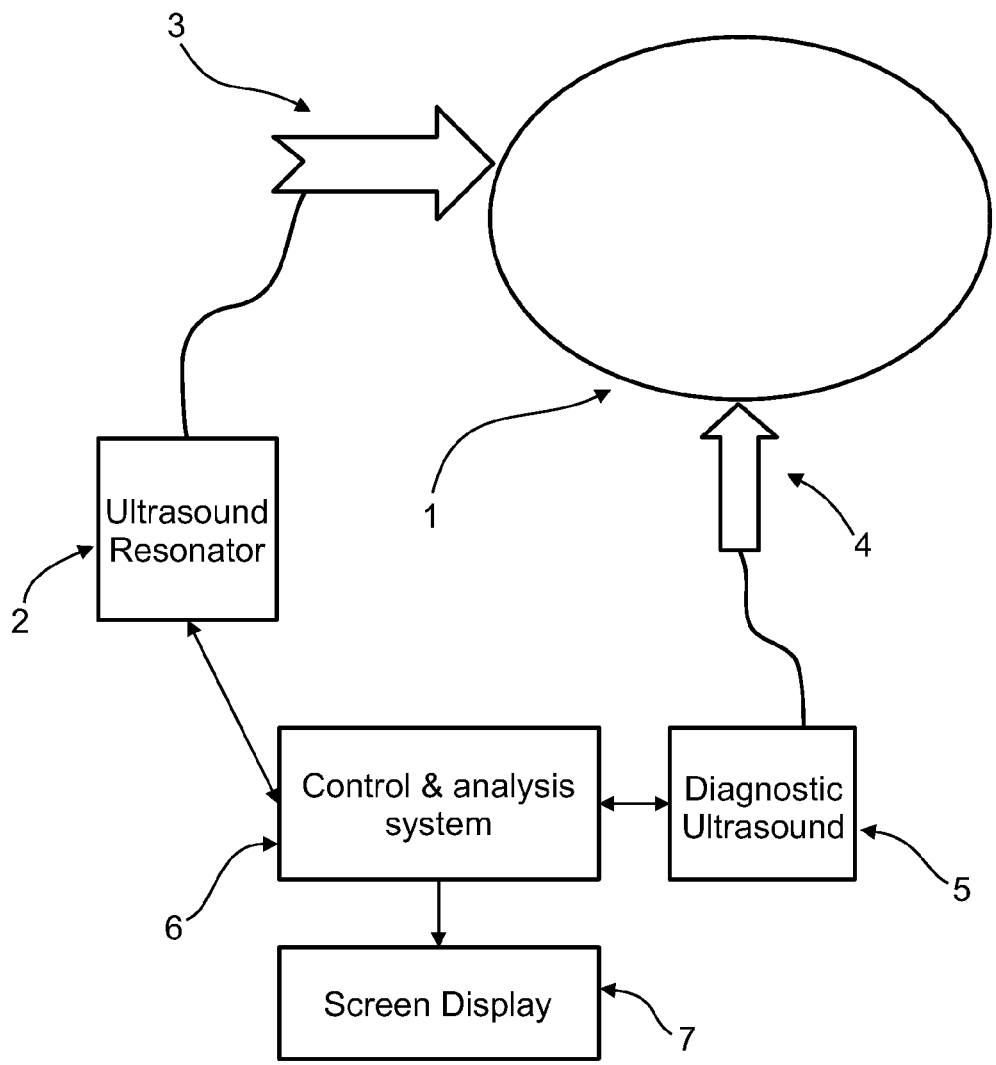
FIG. 1 is a schematic diagram of an apparatus with one form of an Ultrasound Excited Backscatter System, according to an exemplary embodiment of the invention.

An aspect of some embodiments of the invention concerns a method and system for the imaging or identification of tissue type or substance and/or irregularities based on its behavior under ultrasonic heating over time. The system includes an ultrasound resonator for differential heating of different types of tissue, and the same or another ultrasonic device or machine measuring changes in ultrasonic backscatter over time, as a result of tissue heating. In addition, the system includes computer algorithms analyzing ultrasonic backscatter patterns and gradients, as a result of the heating in the examined area over time and location to image the internal subregions of tissues in the examined area. The system is built from single/multiple ultrasonic frequency transmitters, transmitting ultrasonic waves at certain frequency or frequencies, certain amplitude/amplitudes and energy levels. The exposed area is heated; it absorbs some of the ultrasonic energy, and as a result, changes its scattering behavior as a function of the location substance composition and the ultrasound waves mix the area is exposed to, and the duration of this exposure. The system measures ultrasonic backscatter waveforms, their parameters and gradients as they change in time. The computer algorithms compute each location's coefficients from the transmitted ultrasonic parameters, the measurement of the backscatter signals, and their gradients in time. These coefficients may be used for imaging purposes, to compare the coefficients of each location against the other locations to determine irregularities, and/or to analyze behavior of these coefficients to determine tissue types or substance composition or substance levels in the examined locations.

In some embodiments of the invention, instead of or in addition to using backscattering of ultrasound to detect changes in the tissue as a result of heating, specular reflection of ultrasound from the tissue is used, for example as a result of differences in acoustic impedance in the tissue resulting from differential heating.

An aspect of some embodiments of the invention concerns a method of detecting abnormal tissue in a region of healthy tissue, using heating of the tissue, and measurements of backscattering of ultrasound waves from the tissue. Optionally, the to heating is done by ultrasound, either the same ultrasound used for backscattering measurements, or separate heating ultrasound waves. Backscattering of ultrasound waves from the region are measured at least twice, before and after the heating. There may also be additional heating before the first measurement, and/or after the second measurement, and/or during the measurements. The heating may cause abnormal and healthy tissue to change in temperature by different amounts, between the two measurements. Different changes in temperature, in healthy and abnormal tissue in the region, can be distinguished by analyzing the backscattered ultrasound from the region. This may be possible even if the backscattered ultrasound waves are not used, or are not usable, for measuring the temperature or the temperature change absolutely. The different changes in temperature are used to detect the presence and location of the abnormal tissue in the region.

In some embodiments of the invention, changes in characteristics of the backscattered ultrasound, before and after the heating, are used directly to detect the presence and location of abnormal tissue, even without calculating any changes in the temperature. It should be noted that heating of the tissue may cause changes in backscattering characteristics of the tissue even without changing its temperature, for example by causing a phase change in a component of the tissue. Although the description herein generally refers to temperature changes caused by the heating, it should be understood that any change in ultrasound backscattering characteristics, caused by heating, may be used instead for distinguishing abnormal tissue from healthy tissue.

Any of the methods or devices described herein, for distinguishing abnormal from healthy tissue, may also be used for distinguishing any different kinds of tissue, including two different kinds of abnormal tissue, or two different kinds of healthy tissue, or more than two different kinds of tissue.

As used herein, "finding differences" in temperature change, for example for two different locations in the region, includes not only finding the result of subtracting one temperature change from the other, but also includes detecting that there is a difference in two measured temperature changes, to a certain degree of confidence, even without subtracting one from the other, and even if one or both of the measured to temperature changes are sufficiently uncertain that it would not be very meaningful or useful to subtract one from the other.

Different changes in temperature may occur in healthy and abnormal tissue, in response to exposure to heating, because the two types of tissue may be heated at different rates, and/or because the two types of tissue may equilibrate at different rates due to the body's natural thermal equilibration mechanisms. For example, cancerous tissue may equilibrate to body temperature more rapidly after it is heated than normal tissue does, if it is more vascularized than normal tissue. Optionally, differences in heating rate are separated from differences in thermal equilibration rate, by making three of more measurements of backscattered ultrasound at different times. For example, measurements are made before heating, immediately after heating ends, and a few minutes after heating ends, when some thermal equilibration has occurred. Alternatively, measurements may be made before heating, in the middle of heating, and at the end of a heating interval that is comparable to the thermal equilibration time. Measurements may also be repeated with different heating intervals or different heating power, to separate heating rate from equilibration rate. Heating rates may be calculated, independently of thermal equilibration rates, by measuring a temperature change over a heating interval that is short compared to the thermal equilibration time. Alternatively, both heating rate and thermal equilibration rate may be calculated using a model for combined heating and thermal equilibration, with the heating rate and thermal equilibration rate as free parameters, and fitting the model to temperature change measurements at three different times.

If heating is done by ultrasound, then the heating rate of the tissue depends on its ultrasound absorption rate. Heating may also be done by microwaves, radio waves, infrared if it can penetrate far enough into the body, or any other means known in the art, including immersion in a heating bath. Optionally, the heating is done by a means that distinguishes healthy from abnormal tissue, for example by ultrasound at a frequency which is absorbed at a different rate by the healthy and the abnormal tissue. Alternatively, even if heating is done by a means that does not distinguish healthy from abnormal tissue, healthy tissue may be distinguished from abnormal tissue by having a different thermal equilibration rate.

Optionally, the heating power, whether from ultrasound or another source, is distributed relatively uniformly throughout most of the tissue region being examined, so that differences in heating are due substantially to differences in absorption rate in the tissue, rather than being due mostly, or almost entirely, to non-uniform heating power distribution. For example, in the case of heating with ultrasound power or RF power, the incident ultrasound power or RF power varies by less than a factor of 2, or less than 30%, or less than 20%, or less than 10%, over the tissue region. Optionally, in a plane normal to the incidence of the power, the tissue region is at least 3 cm×3 cm, or at least 5 cm×5 cm, or at least 10 cm×10 cm, in cross-section, and extends over a distance, in the direction of incidence of the power, of at least 1 cm, or at least 2 cm, or at least 5 cm, or at least 10 cm.

In some embodiments of the invention, instead of heating the tissue, it is cooled, optionally before any measurements are made of backscattered ultrasound. Consequent warming of the tissue to thermal equilibrium, as a function of position, is measured at at least two different times, by analyzing measurements of backscattered ultrasound, and differences in the thermal equilibration rate are used to distinguish the healthy tissue from the abnormal tissue. The analysis need not calculate temperatures at each time, but optionally uses changing characteristics of the backscattered ultrasound directly to find thermal equilibration times.

Optionally, if ultrasound heating is used, the ultrasound absorption rate is calculated from the increase in temperature resulting from applying a given heating ultrasound heating power to the region, taking into account a decrease in incident ultrasound power going across the region in the direction of propagation of the ultrasound, due to absorption and scattering of ultrasound as it traverses the tissue. Similar considerations apply if other types of waves are used for heating, such as microwaves.

Healthy tissue and abnormal tissue may be further distinguished by repeating measurements using different frequencies of heating ultrasound, for which the ratio of absorption rate in healthy and abnormal tissue may differ, and a similar method may be used for microwave heating or heating with other types of waves. Even if the backscattered ultrasound is barely adequate for distinguishing the temperature change in healthy and abnormal tissue, they may be distinguished with more reliability if to differences between them are detected using a plurality of different parameters, for example equilibration rate, and absorption rate at two or more different ultrasound frequencies.

Optionally, if the diagnostic ultrasound used for backscattering measurements is separate from the heating ultrasound, in a case where ultrasound heating is used, then no heating ultrasound is used during the backscattering measurements, which has the potential advantage of avoiding interference from reflected or scattered heating ultrasound in measuring the generally weaker signal from the backscattered diagnostic ultrasound. Alternatively, if the ultrasound heating begins before at least one of the measurements of backscattering, and continues after that measurement, then it is not interrupted for that measurement, though optionally it is reduced in power during the measurement.

Optionally, the measurements and analysis of backscattered ultrasound are sensitive enough to detect a volume of abnormal tissue that is 1 cm in diameter in its shortest dimension, which increases in temperature by an amount that differs by a factor of 3 from normal tissue surrounding it, with 90% confidence for example. This sensitivity is optionally present when, for example for safety reasons, the maximum increase in local temperature in the region is kept below 4 degrees Celsius, or below 3 degrees, or below 2 degrees, or below 1 degree. This sensitivity is also optionally present when, for example for safety reasons, the power of the heating ultrasound is kept below regulatory limits for diagnostic ultrasound, for example below any of the power limits listed above. Optionally, the measurements and analysis of backscattered ultrasound are sensitive enough to detect differences in temperature change, between the healthy and abnormal tissue, of less than 2 degrees Celsius, or less than 1 degree, or less than 0.5 degree. Optionally, the measurements are sensitive enough to measure temperature change absolutely, in the abnormal tissue and/or in the healthy tissue, to within 2 degrees, or 1 degree, or 0.5 degrees.

Optionally, the heating ultrasound, or heating power from another source, is used for a duration that is short compared to a typical thermal equilibration time, or for an interval comparable to or greater than a typical thermal equilibration time in tissue. For example, the heating duration is less than 1 minute, or between 1 and 2 minutes, or between 2 and 3 minutes, or between 3 and 5 minutes, or more than 5 minutes.

Optionally, the measurement of backscattered ultrasound comprises measuring one or more characteristics, for example a standard deviation, of a distribution of amplitudes of backscattered power from different closely spaced locations in the heated region. Such measurements can be used to estimate temperature change, or at least to detect qualitative differences in temperature change from different parts of the region, using methods similar to those described by Arthur et al, cited above. Additionally or alternatively, the measurement of backscattered ultrasound comprises measurements of a shift in harmonic frequency of ultrasound scattered by a semi-regular lattice structure in the tissue, which can be used to estimate temperature, or at least to detect qualitative differences in temperature change from different parts of the region, using methods similar to those described by Seip and Ebbini, cited above. Optionally, both methods are used to estimate temperature changes from the backscattered ultrasound.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 illustrates a system for medical imaging of soft tissue. The system includes an Ultrasonic resonator (2) for heating tissues of the examined area of the patient (1). The resonator (2) is connected to a transducer (3) which is attached to the body of the patient (1), and induces ultrasonic power at a determined wave mix of frequencies, amplitudes, and energy levels. As the ultrasound waves propagate through the body tissues, their energy is absorbed in the tissues as a function of the tissue type and substance composition. Each tissue type, changes its ultrasonic behavior, and specifically its scattering behavior in response to the heating. A second ultrasound device (5), of diagnostic ultrasound characteristics, is connected to a second transducer (4), diagnosing the ultrasonic signal from the examined area. As the tissues examined absorb the energy, the backscatter pattern and energy of the diagnostic ultrasound signal may change, depending on the tissue type and/or substance composition at each location of the examined organ. A controller (6), for example a computer, calculates parameters at each location and time from the backscattering behavior related to that location, and accordingly optionally displays in the display (7), to or another output device, a 2D or 3D or 4D image of the diagnosed area. The display optionally identifies locations in the tissue that appear to be abnormal, or possibly abnormal, based on their backscattering behavior, including cancerous tissue for example. Controller (6) also optionally controls the timing and operating parameters of resonator (2) and/or device (5). In some embodiments of the invention, one or more of the different functions of the controller are located in physically separate units, but the units are still referred to collectively as "the controller."

Figure 2:
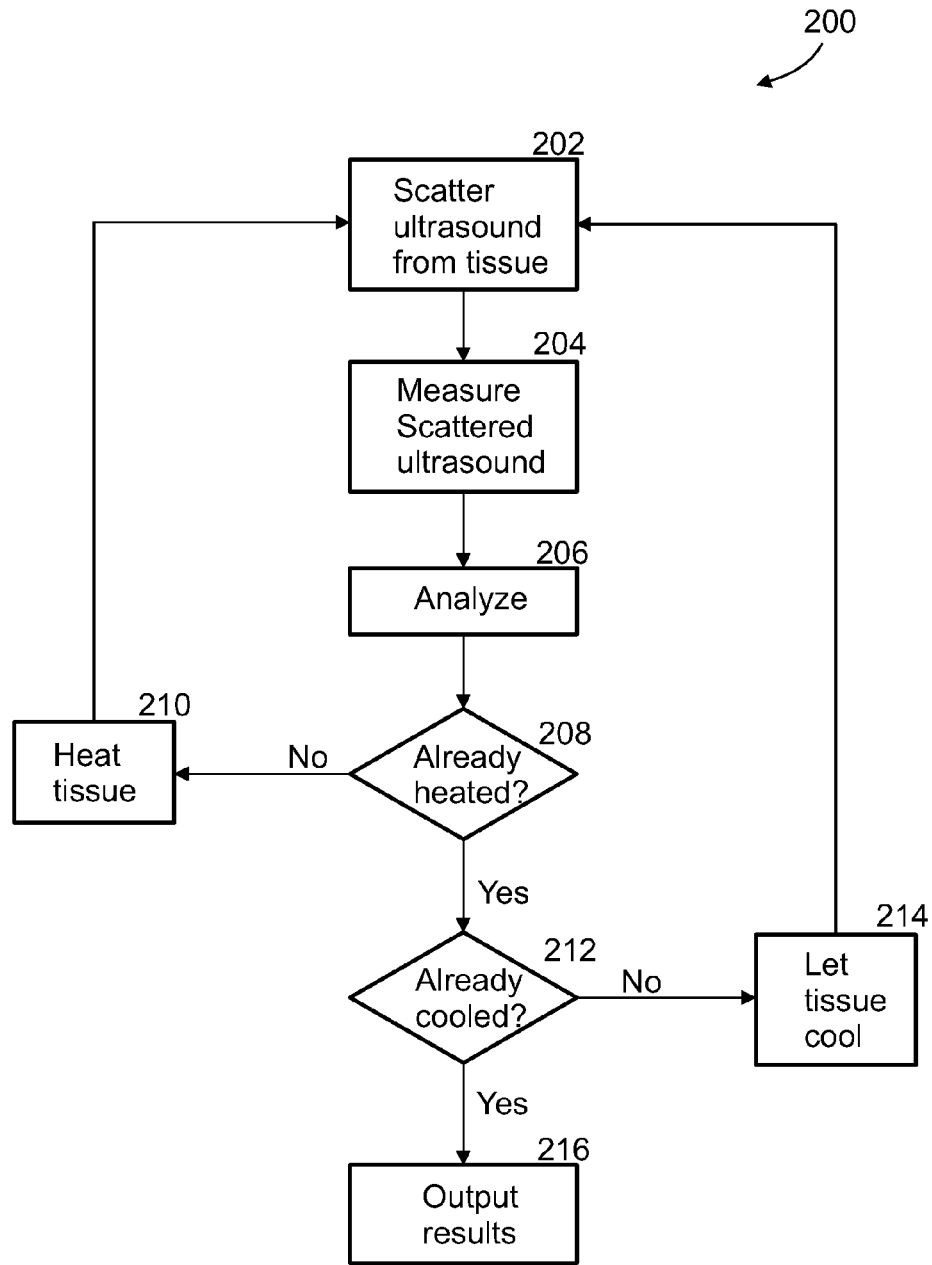
FIG. 2 shows a flowchart for a method of detecting abnormal tissue in a region of healthy tissue, using ultrasound backscattering, according to an exemplary embodiment of the invention.

FIG. 2 shows a flowchart 200 for a method of detecting abnormal tissue in a region of healthy tissue, using ultrasound backscattering, according to an exemplary embodiment of the invention. At 202, ultrasound is scattered from the tissue, and the scattered ultrasound is measured at 204, and the results are analyzed and recorded at 206, for example to provide an indication of the temperature as a function of position in the tissue. If the tissue has not already been heated, or the heating has not been finished, then a decision is made at 208 to heat the tissue, or to further heat the tissue, at 210. Scattering of ultrasound from the tissue at 202, measuring the scattered ultrasound at 204, and analyzing and recording the results at 206, are then repeated after the heating, or after the additional heating, when the temperature is higher. Optionally these actions are repeated more than once, for example to provide an indication of the change in temperature as a function of position after different degrees of heating, or over different time intervals. If the abnormal tissue has a different heating rate than the healthy tissue, for example a different ultrasound absorption rate if the heating is done by ultrasound, then the abnormal tissue will generally undergo a different temperature change as a result of the heating, than the healthy tissue, at least if the heating is done over a time interval short compared to the thermal equilibration time.

If the heating is finished, then at 212 a decision is made as to whether the tissue has already been cooled, and if the cooling process has finished. If not, then at 214 the tissue is allowed to cool, or to cool further. Optionally, the tissue is cooled passively. Alternatively, the tissue is cooled actively. Scattering ultrasound from the tissue at 202, measuring the scattered ultrasound at 204, and analyzing and recording the results at 206, are repeated after the tissue has been allowed to cool. Optionally, these actions are repeated more than once, for example to measure the temperature as a function of to position for different time intervals relative to the thermal equilibration time. If the abnormal tissue has a different thermal equilibration rate than the healthy tissue, for example because it has a different degree of vascularization, then the temperature change during the cooling will be different for the abnormal and healthy tissue.

If the cooling of the tissue has been completed, then at 216 the results of the measurements are outputted. For example, the results may show the temperature as a function of position at two or more times before, after, and during the heating, as well as at two or more times before, after, and during the cooling. This information may be used, for example, to find the ultrasound absorption rate and the thermal equilibration time of the tissue, as a function of position. That information, in turn, may make it possible to detect and/or characterize abnormal tissue. For example, cancerous tissue may have a different ultrasound absorption rate, and a shorter thermal equilibration time, than normal tissue, due to different cellular composition and a greater degree of vascularization than normal tissue.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments to and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for detecting a tissue surrounded by a different tissue in a region, the method comprising:
    a) making a first measurement of ultrasound backscattered from the region;
    b) heating the region, at least after the first measurement, using incident ultrasound heating power, RF heating power or both, causing the temperature of each point in the region to rise by no more than 4 Celsius;
    c) making one or more additional measurements of ultrasound backscattered from the region after some or all of the heating; and
    d) analyzing the measurements, using uniformity of the incident heating power to detect the tissue by finding one or both of differences in changes in temperature and differences in thermal expansion, caused by the heating, between the tissue and the surrounding different tissue; wherein the region has a cross-section of at least 3 cm by 3 cm perpendicular to the direction of incidence of the power, and extends over a distance of at least 1 cm in the direction of incidence of the power.

2. A method according to claim 1, wherein the heating heats both a tissue in the region that is no more than 1 centimeter in diameter in its shortest dimension, and a different surrounding tissue in the region, so that the two tissues expand due to the heating by amounts that differ from each other, and the measurements and analysis detect the different amounts of expansion, to distinguish the two tissues.

3. A method according to claim 1, wherein analyzing comprises calculating one or more characteristics of a distribution of amplitudes of backscattered ultrasound as a function of position from which it is scattered.

4. A method according to claim 1, wherein analyzing comprises calculating a frequency shift of backscattered ultrasound as a function of position from which it is scattered.

5. A method according to claim 1, wherein heating comprises heating with ultrasound.

6. A method according to claim 5, wherein heating with ultrasound comprises using ultrasound generated by a different ultrasound transducer than a transducer used to generate the backscattered ultrasound measured in the first and additional measurements.

7. A method according to claim 6, also comprising not running the transducer used to generate the ultrasound used for heating, while making the first and additional measurements.

8. A method according to claim 5, wherein heating comprises using ultrasound power that does not exceed spatial peak temporal-average (Ispta) of 720 mW/cm^2.

9. A method according to claim 1, wherein analyzing the measurements finds differences in the temperature change, at different positions in the region, of less than 2 degrees Celsius, with a spatial resolution of 1 centimeter or better.

10. A method according to claim 9, wherein the calculated differences in the temperature change, for at least some different positions in the region, are accurate to within less than 2 degrees Celsius, with a spatial resolution of 1 centimeter or better.

11. A method according to claim 1, wherein making one of more additional measurements comprises making at least two additional measurements, and analyzing comprises calculating an ultrasound absorption rate and a thermal equilibration rate as a function of position in the region.

12. A system for detecting at least one type of abnormal tissue in a region of healthy tissue, comprising:
   a) a diagnostic ultrasound transducer and detector;
   b) a tissue heating element, the same as or different from the diagnostic ultrasound transducer, for heating tissue; and
   c) a controller programmed to:
      i) control the tissue heating element to heat the tissue in the region by less than 4 degrees Celsius;
      ii) control the diagnostic ultrasound transducer and detector to make at least two measurements of backscattered ultrasound from the region, respectively before and after at least one time interval when the tissue heating element is heating the tissue in the region;
      iii) analyze results of the measurements, using uniformity of the heating power to find differences, at different positions in the region, in one or both of the change in temperature and the thermal expansion, from before to after the time interval, that distinguish that type of abnormal tissue from the healthy tissue; and
      iv) using the differences to identify which parts of the region are the abnormal tissue and which are healthy tissue.
   wherein the tissue heating element comprises an ultrasound transducer, an RF antenna, or both, and the tissue heating element is adapted to heat a region with cross-section of at least 3 cm by 3 cm perpendicular to the direction of incidence of the power, and extending over a distance of at least 1 cm in the direction of incidence of the power.

13. A system according to claim 12, wherein the tissue heating element comprises an ultrasound transducer, the same as or different from the diagnostic ultrasound transducer.

14. A system according to claim 13, wherein the tissue heating element is different from the diagnostic ultrasound transducer.

15. A system according to claim 12, wherein the controller is programmed to use the differences in one or both of a heating rate of the tissue, and a temperature equilibration rate of the tissue. differences in one or both of a heating rate of the tissue, and a temperature equilibration rate of the tissue.

16. A system according to claim 15, wherein the controller is programmed to use the differences in the temperature change to find differences in both the heating rate of the tissue, and the temperature equilibration rate of the tissue.

* * * * *